(12) United States Patent
Andle et al.

(10) Patent No.: US 7,800,285 B2
(45) Date of Patent: Sep. 21, 2010

(54) COATING FOR HARSH ENVIRONMENTS AND SENSORS USING SAME

(75) Inventors: Jeffrey C Andle, Falmouth, ME (US); Reichl B Haskell, Nashua, NH (US); John H. Bradshaw, Atkinson, NH (US)

(73) Assignee: Delaware Capital Formation, Wilmington, DE (US)

( * ) Notice: Subject to any disclaimer, the term of this patent is extended or adjusted under 35 U.S.C. 154(b) by 689 days.

(21) Appl. No.: 11/814,167

(22) PCT Filed: Apr. 20, 2006

(86) PCT No.: PCT/US2006/015537
§ 371 (c)(1),
(2), (4) Date: Jul. 17, 2007

(87) PCT Pub. No.: WO2007/123539
PCT Pub. Date: Nov. 1, 2007

(65) Prior Publication Data
US 2010/0038997 A1    Feb. 18, 2010

(51) Int. Cl.
*H01L 41/09* (2006.01)
*H03H 9/15* (2006.01)
(52) U.S. Cl. .................. 310/340; 310/313 R; 310/320
(58) Field of Classification Search ............. 310/313 R, 310/320, 340
See application file for complete search history.

(56) References Cited

U.S. PATENT DOCUMENTS

| | | | | |
|---|---|---|---|---|
| 5,440,189 | A * | 8/1995 | Nakahata et al. | 310/313 R |
| 5,880,552 | A * | 3/1999 | McGill et al. | 310/313 R |
| 6,320,295 | B1 | 11/2001 | McGill et al. | |
| 2004/0076081 | A1 | 4/2004 | Menzel et al. | |
| 2006/0103486 | A1 * | 5/2006 | Ruile et al. | 333/133 |
| 2007/0228876 | A1 * | 10/2007 | Sung | 310/320 |
| 2009/0309453 | A1 * | 12/2009 | Andle | 310/313 R |

FOREIGN PATENT DOCUMENTS

EP    0440384 A1    8/1991

OTHER PUBLICATIONS

McGill R A et all: Performance optimization of surface acoustic wave chemical sensors, IEEE Transactions of ultrasonics, ferroelectrics and frequency control, vol. 45 No. 5, Sep. 1998 pp. 1370-1380, XP 000801811, ISSN 0885-3010 sections II.A, II.D, III.C.

Mirajami Kiuru, "Experimental Studies on Diamond-Like Carbon and Novel Diamond-Like Carbon-Polymer-Hybrid Coatings" University of Helsinki, Helsinki, Finland, HU-P-D115, Aug. 20, 2004.

N. Schuhler , P. Oelhafen, "Ion beam deposition of a-C:H on niobium and tungsten: in situ investigations using photoelectron spectroscopy" Surface Science 365 (1996) 817-824, 0039-6028/96/ Elsevier Science B.V. PII S0039-6028 (96)00749-2, 1996.

Daniel Nillson, "Synthesis and evaluation of TaC:C low friction coatings" , Dissertation presented at Uppsala University, Oct. 1, 2004, Acta Universitatis Upsalientis, Uppsala, Sweden, 2004.

* cited by examiner

*Primary Examiner*—Thomas M Dougherty
(74) *Attorney, Agent, or Firm*—Shalom Wertsberger; Saltamar Innovations

(57) ABSTRACT

A coating providing high abrasion and chemical resistance composed of a barrier layer from vanadium, molybdenum, niobium, tantalum and the like, and an outer layer of diamond-like carbon. The coating is especially applicable for acoustic wave device (AWD) based sensors, and for passivating an electrode such as an electrode deposited on the AWD sensing area. The coating provides excellent mechanical and acoustical characteristics for coating acoustic wave devices allowing the sensor to operate in harsh environments.

15 Claims, 1 Drawing Sheet

COATING FOR HARSH ENVIRONMENTS AND SENSORS USING SAME

FIELD OF THE INVENTION

Figure 1:
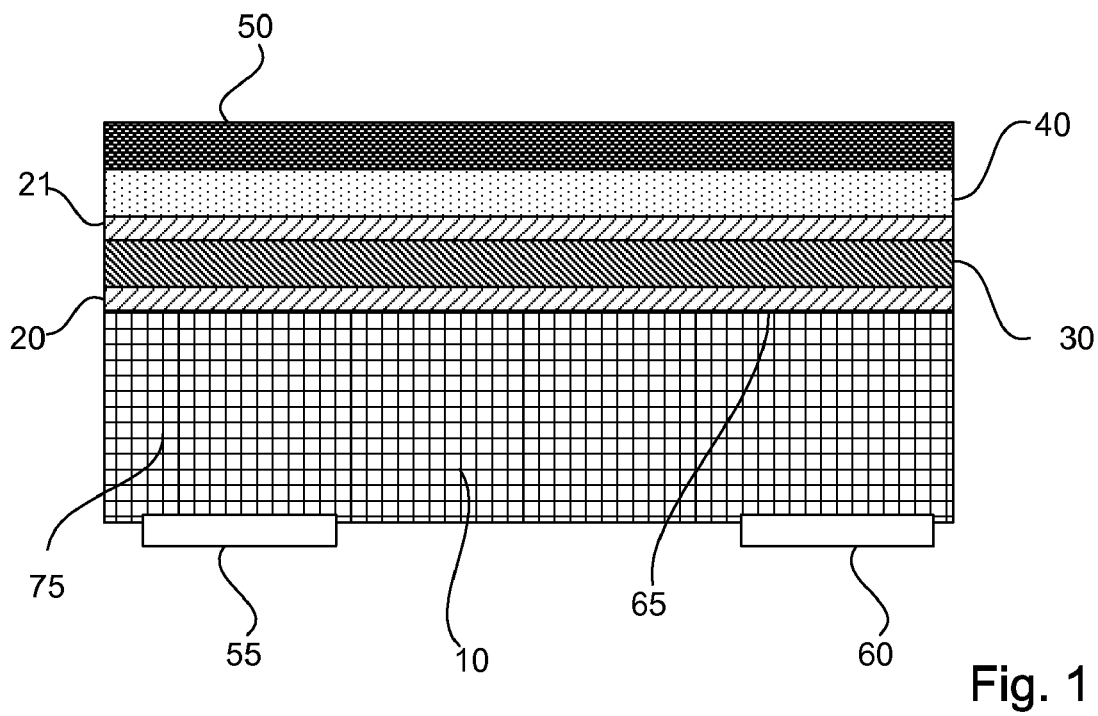

This invention relates generally to making sensors for harsh environments, and more particularly to coatings sensors with diamond-like carbon for operation in harsh physical or chemical environments.

BACKGROUND OF THE INVENTION

The need to operate sensors in harsh environments is common. Examples include sensors, switches, and the like, which are designed to operate in abrasive environments, in corrosive chemicals, and the like. Oftentimes the long term sensor operation is hindered by the continued contact the environment. The problem is particularly severe in the field of electro acoustic sensors, also known as Acoustic Wave Devices. Thus the present specifications will relate to the application of a coating to mitigate the problems associated with such operations, primarily by using the AWD sensor. The skilled in the art will recognize the applicability of the coating to other devices.

Piezoelectric sensors are well known. They are used for sensing material properties such as viscosity and density, for detecting the presence of certain materials in an environment, for measuring purity of fluid substance, and the like. Structures known for acoustic sensing range from the simple crystal resonator, crystal filters, acoustic plate mode devices, Lamb wave devices, and others. Briefly, these devices comprise a substrate of piezoelectric material such as quartz, langasite or lithium niobate, or thin films of piezoelectric material, such as aluminum nitride, zinc oxide, or cadmium sulfide, on a non-piezoelectric substrate. The substrate has at least one active piezoelectric surface area, which is commonly highly polished. Formed on the surface are input and output transducers for the purpose of converting input electrical energy to acoustic energy within the substrate and reconverting the acoustic energy to an electric output signal. These transducers may consist of parallel plate (bulk wave) or periodic interdigitated (surface-generated wave) transducers. Each sensor has at least one sensing area which is exposed to the environment being measured. The interaction between the surface and the environment causes measurable changes in the electrical characteristics of the sensor. The sensors may be used for sensing density, viscosity, and other such physical parameters.

Piezoelectric devices are generally manufactured from hard, crystalline materials. However, even those surfaces change when exposed to certain chemicals or abrasives. Piezoelectric based sensors are very susceptible to changes in the sensing area. Thus their use was so far limited to environments that will not damage such surfaces. Damage may be chemical such as etching, or mechanical such as abrasion. Therefore the usability of such sensors in environments like oil wells measuring of characteristics of drilling mud or oil, sensing characteristics of ink, melted polymers, and similar abrasive materials was heretofore limited as the sensors will suffer from high variability over time. Other environments which can harm such sensors are chemically reactive materials such as strong acids and bases used in polymer processing, pulp and paper processing, and other industrial and chemical processes. Furthermore, the need for a conductive electrode or shield layer in the most desirable sensor topologies introduces a further susceptibility to chemical attack and/or abrasion as virtually all metals have one or more chemical susceptibility and or are soft, abrasion prone materials. A further common requirement to liquid phase sensing is that the sensing surface be sufficiently smooth. Many liquid phase AWD sensors require nanometer or lower average roughness.

The electrodes that are deployed in the most desirable sensor topologies are commonly made of gold (Au) deposited by any convenient method. In many cases the electrode have to be electrically insulated from the environment.

Insulating surfaces, devices, electrodes, and the like, from an hostile environment is commonly done by coatings the likes of plastic, glass or similar materials. However such coatings often interfere with the operation of the sensor. For example in an AWD type sensor, the coating must have acoustic qualities that will not significantly impede the sensor operation, as well as the desired hardness, toughness, electrical characteristics, and the like. Plastics and glass incur excessive damping and are not always chemically resistant, nor are they sufficiently hard.

Diamond Like Carbon, or DLC hereinafter, is well known coating material. DLC enjoys high hardness and therefore high resistance to abrasion, it may be smoothly applied, and generally provides an excellent coating layer whose thickness may be tailored to need. DLC is deposited using common methods such as vaporizing, ion implanting, and the like.

Certain materials do not adhere well to each other. DLC suffers from poor adhesion to materials like gold, platinum, silver, most oxides, and many other materials, especially piezoelectric materials commonly used in AWD sensors and the like. Therefore, while the DLC clearly provides the required abrasion resistance, providing adequate adhesion between a DLC layer and a piezoelectric material or an electrode deposited on such piezoelectric material presents a problem. In other cases, different coating materials exhibit undesirably large ion migration problems which adversely effect electrical or acoustic characteristics of the desired coating.

Implantable medical devices have been demonstrated with relatively thick (in the order of several to several hundred microns) coatings of DLC, on thin (a few nanometers) adhesion layers, as shown in "EXPERIMENTAL STUDIES ON DIAMOND-LIKE CARBON AND NOVEL DIAMOND-LIKE CARBON-POLYMER-HYBRID COATINGS" Mirjami Kiuru, PhD Dissertation, University of Helsinki (2004). Typical substrates for such coatings are refractory metal parts such as titanium hips. When these coatings are applied to semiconductor devices the films are extremely unreliable. These coating films often suffer from delaminate and in some cases cause breakage of the silicon substrates.

Therefore, there exists a continuing and yet unresolved need for a sensor capable of continued operation in broad range of chemical, thermal and mechanical harsh environments.

It is therefore an object of the present invention to provide a coating that will provide the above mentioned characteristics when applied to a sensing area of a sensor. Since no single material offers all of the ideal properties, many applications will ultimately require a series of layers, relaxing the requirements of the individual layers but further requiring compatibility amongst the layers. Preferably the coating should be sufficiently smooth to address fluid-phase sensor applications.

Many such acoustic sensors utilize an electrode on the sensing surface, and the coating provided by the present invention is particularly beneficial to such sensors. The skilled in the art will recognize that the term electrodes may relate to ground electrodes, transducers (especially in the case of actively driving or driven electrodes), other structures that cause perturbation or reflection in the piezoelectric crystal, or other conductors that either carry electrical energy or deliver it to a predetermined point.

An additional objective of the present invention is to provide the sensor with a smooth (preferably nanometer scale) sensing surface with excellent abrasion resistance, excellent chemical resistance and the ability to withstand temperature extremes from −50° C. to +350° C. Suitable coatings include alloys of silicon-aluminum oxynitride (SiAlON) including the extremes of silicon nitride, aluminum oxide and the like, amorphous boron nitride, amorphous and nanocrystalline carbon, boron carbide (including the like of boron doped diamond and boron doped DLC), and $\beta$-$C_3N_4$. All of these materials offer abrasion resistance and thermal stability with varying degrees of chemical resistance.

Of these coatings, so-called diamond-like carbon (DLC) is found to offer the best properties of surface smoothness, chemical resistance and abrasion resistance. While there is considerable debate as to an exact definition of diamond-like, for the purposes of the present invention it shall be taken to imply all films with a molar percentage of greater than 75% carbon and having mixed chemical bonding state of graphitic ($sp^2$) and diamond ($sp^3$). It should be noted that the term also extend to various modification of diamond-like carbon, such as boron-doped diamond (BDD), carbon-rich refractory metal carbides, and the like.

Diamond-like carbon is well-adhered to metals that form carbides, such as tungsten, molybdenum, tantalum, niobium, vanadium, hafnium, zirconium, titanium, and chromium in increasing order of typical adhesive strength. These metals are traditionally used in so-called adhesion layers. The adhesive strength of these metals is in direct proportion to their ability to inter-diffuse and alloy with adjacent materials.

Inter-diffusion of the adhesion layer into the DLC film is undesirable since it leads to unstable film properties and poor aging characteristics. It is especially desired that the underlying metal have low mobility in the carbon and that metal will have low mobility into the carbon, a condition that may become critical at high temperatures. Therefore by way of example, while titanium and zirconium offer excellent adhesion, they are excessively mobile in carbon and vice versa at high temperatures. On the other hand tungsten is an excellent barrier metal (has low mobility and prevents other atoms from diffusing into or through it); however tungsten has the poorest adhesion. Niobium and tantalum are the preferred metals for a barrier/adhesion layer under diamond-like carbon.

Niobium and tantalum offer good chemical resistance and excellent adhesion of the outermost DLC layer. Both materials are sufficiently conductive for shielding but are inadequate for many electrode requirements. In these cases an innermost layer of a thermally stable material with chemical resistance and high conductivity is required. Although aluminum is frequently employed as an electrode material it is chemically active and highly mobile at elevated temperatures. The preferred metals are gold and platinum, although silver and palladium are also acceptable for some preferred embodiments. Platinum has the most favorable properties while gold is more commonly employed. Ruthenium, Rhodium, Rhenium, Osmium and Iridium may also prove desirable in specific applications.

Applying the coating to a piezoelectric material presents yet another problem stemming from the extremely high film stresses associated with DLC and the significant mismatch of thermal expansion between DLC and such metal or piezoelectric materials as are commonly employed. The preferred embodiment of the present invention therefore utilizes application of a relatively thin DLC coating (of less than 1 µm) and a thicker adhesion/barrier metal system than is traditionally employed (of about 200 nm).

The adhesion of tantalum to gold or platinum and of the electrode to the piezoelectric substrate can be improved through a thin adhesion layer of chromium or titanium. The most preferred embodiment would consist of a thin (Circa 10 nm) titanium, zirconium or chromium layer, a conductive (50-200 nm) gold or platinum electrode layer, another thin (Circa 10 nm) titanium, zirconium or chromium layer, a barrier layer (25-300 nm) of niobium or tantalum, and a surface of DLC (10-500 nm).

The exact composition of the DLC is a matter of choice. Prior art in thin film development suggest numerous dopants or surface treatments ranging from several parts per million to several percent of nitrogen or various metals. Details of thin film may be found in "Synthesis and Evaluation of TaC:C Low-Friction Coatings", Daniel Nilsson, Ph.D. Dissertation, ACTA Universitatis Upsaliensis (2004). Fluorine dopants have been considered from trace levels through 67 atomic percent (perfluoroalkanes). The abrasion and chemical resistance of such films appear best when the atomic percent carbon is maximized.

Films with only 33% carbon include the limit of hydrocarbons and fluorocarbons (e.g. Teflon®) and have no abrasion resistance. Films in the range of 33% to 66% carbon are characteristic of carbide alloys. These films are extremely hard but are not as chemically resistant or as thermally stable as DLC. In many cases the surfaces are not as smooth as true DLC. Thus only films containing approximately 67% or higher percentage carbon in their bulk are specifically considered as "DLC" herein. Our experience with tantalum-doped and fluorine-doped films indicates that the film should preferably have in excess of 90% carbon and the most preferred embodiment has in excess of 97% carbon.

While chemical resistance and passivation generally favor an insulating layer as is obtained by pure carbon DLC, certain sensor applications using carbon electrodes in electrochemical sensors, notably electrochemical-AWD hybrids, require a conducting DLC layer. Boron doped ($\sim 10^{19}$ $cm^{-3}$, consistent with silicon doping levels, up to 1% B; 99% C) diamond is a suitable material for use in electrochemical and/or acoustic sensors, and is considered as a type of DLC.

A further object of the invention includes the ability to attach chemically selective probes to the DLC surface.

Thus in one aspect of the present invention there is provided a coated Acoustic Wave Device (AWD) based sensor, the sensor having at least one piezoelectric plate having two opposing faces, one of said faces having a sensing area, the sensor having a coating applied to the sensing area, the coating characterized by: a first electrode disposed on the sensing area; a barrier layer disposed over the first electrode, the barrier layer comprising at least one metal selected from the group consisting of tantalum, niobium, vanadium, molybdenum, or a combination thereof; and an abrasive resistant layer comprising Diamond-Like Carbon (DLC) disposed over the barrier layer.

Optionally the coating further comprises an adhesion layer disposed between the barrier layer and the electrode. Further optionally another adhesion layer may be disposed between the electrode and the sensing face. The adhesion layers may be titanium, zirconium, chromium, vanadium, niobium, tantalum, molybdenum, or a combination thereof.

Preferably the first electrode comprises a metal selected from a group consisting of platinum, palladium, gold, silver, copper, aluminum, osmium, iridium, or a combination thereof. Optionally the DLC may be boron doped diamond. Further optionally, chemically selective probes are coupled to the DLC.

In a preferred embodiment of the present invention there is provided a coated acoustic wave device sensor as described above, having a second electrode disposed on the face opposite the face comprising the sensing area, forming a parallel plate resonator with said first and second electrodes. Optionally, a third electrode is disposed on the face opposite the face comprising the sensing area, wherein the first and second electrodes form an input parallel resonator, acting as an input transducer, the first and third electrode also form an output parallel resonator, acting as an output transducer; wherein the input and output resonators being sufficiently close to couple acoustic energy from the input resonator into the output resonator, for forming a multi-pole coupled resonator filter.

In another aspect of the present invention there is provided a method of passivating an electrode, the method characterized by the steps of:

depositing a barrier layer onto said electrode, the barrier layer comprising at least one metal selected from the group consisting of tantalum, niobium, vanadium, molybdenum, or a combination thereof; and, depositing an abrasive resistant layer comprising Diamond-Like Carbon (DLC) onto said barrier layer.

Optionally the method further comprises the step of depositing an adhesion layer between the electrode and the barrier layer. Most preferably the electrode is coupled to an acoustic wave device based sensor. Optionally, the method further comprise the step of coupling chemically selective probes to the DLC layer.

SHORT DESCRIPTION OF DRAWINGS

The summary above, and the following detailed description will be better understood in view of the enclosed drawings, which depict details of preferred embodiments. It should however be noted that the invention is not limited to the precise arrangement shown in the drawings and that the drawings are provided merely as examples.

FIG. 1 depicts a simplified elevation cross section view of an acoustic sensor utilizing a coating in accordance with the most preferred embodiment of the invention.

Figure 2:
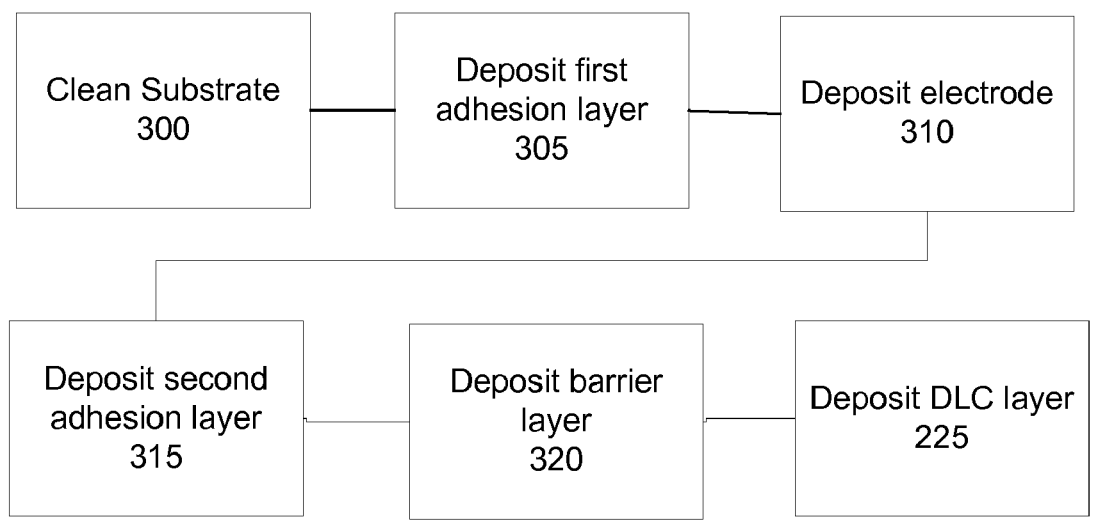

FIG. 2. depicts a process for coating a sensor in accordance with the preferred embodiment of the invention.

DETAILED DESCRIPTION

An important objective of the present invention is to provide AWD and other sensors with a smooth (nanometer scale) surface with excellent abrasion resistance, excellent chemical resistance and the ability to withstand a wide range of temperatures, with the range from −50° C. to +350° C. being most preferred. While an aspect of the invention relates to coating piezoelectric material directly, a preferred embodiment relates to coating one or more electrodes deposited on the piezoelectric material. FIG. 1 depicts a cross-section of such preferred sensor 75.

The most preferred sensor geometries require electrodes of excellent electrical characteristics on the sensing area. In those geometries an innermost electrode layer 30 of a thermally stable material with chemical resistance and high conductivity is deposited on the sensing face 65 or a portion thereof. Silver and palladium are examples that offer such characteristics, but the preferred embodiment uses gold or platinum. Platinum has the most favorable properties while gold is more commonly employed. Other candidates include ruthenium, rhodium, rhenium, osmium, and iridium which have the requisite thermal stability and varying environmental stability and conductivity properties. Notably, the electrode layer need not extend to the entire sensing area, and the electrode layer is not necessarily used as an electrode, i.e. it is not necessarily electrically connected to any parts of the sensor circuitry.

Diamond-like carbon is well-adhered to metals that form carbides, such as tantalum (Ta), niobium (Nb), vanadium (V), hafnium (Hf), zirconium (Zr), titanium (Ti), tungsten (W), molybdenum (Mo) and chromium (Cr) by way of non-limiting example. However it does not adhere well to gold, platinum, oxides, or most piezoelectric materials. Therefore, the present invention contemplates an intermediate barrier layer of carbide forming metal, such as those described above. The barrier layer 40 lies between an outer layer 50 and the sensing face 65 of the base material 10 to be coated, and if an electrode layer is used, the barrier layer overlies the electrode layer. In addition to providing good adhesion and enhanced protection to the electrode layer and/or the piezoelectric material, the barrier layer also acts as a matching medium to match the thermal expansion and film stresses of the DLC with the layers below the barrier layer.

For clarity, in these specifications the term outer layer will relate to a coating layer of high abrasion material as described above. It is important however to realize that other coating layers, either of DLC or other materials, may be overlaid on top of the 'outer layer' 50, and the term 'outer' should be construed broadly only as relating to the layer interfacing with the barrier layer 40 away from the base material 10. This interface may be direct or indirect as described below.

To obtain the best coating stability, the underlying barrier layer preferably has low mobility in the carbon, and the carbon has low mobility into the barrier layer. This is an important consideration at high temperatures. Therefore, niobium and tantalum are the preferred metals for a barrier layer under diamond-like carbon. The use of vanadium (V) is also contemplated as a barrier metal since it is in the same column of the periodic table and molybdenum (Mo) is contemplated since refractory metal properties often track along a diagonal rather than vertically. A thin carbide alloy interface which is stable against diffusion over wide temperature ranges, is formed between these metals and the DLC layer. These metals are less reactive with carbon than are titanium, zirconium and chromium but are more adherent than tungsten.

An additional benefit stemming form the use of niobium or tantalum is that the volume of NbC and TaC are comparable to the sums of the volumes of the metal and carbon. In contrast, titanium, zirconium and chromium form carbides with shorter bond lengths than the bulk metal and bulk carbon, causing an evolving dimensional change as the metal and carbon inter-diffuse and carbide is formed. The preferred embodiment therefore enjoys dimensional stability in the thin film over long periods of time at high temperatures. It is noted that in certain embodiments a niobium or tantalum layer may act as an electrical shield, however it generally does not provide sufficient and stable electrical conductivity to act as good electrodes. This effect relates to the partial oxidization of the metal as it is deposited and the associated film resistance.

The adhesion of the intermediate layer 40 to the electrode layer 30, and of the electrode layer to the base material 10 may be improved by depositing an optional thin adhesion layer of chromium, zirconium or titanium. The adhesion layer 20 may be deposited only between barrier layer 40 and electrode 30, or as shown by adhesion layer 21 between the electrode and the sensing area 65, or preferably both.

Thus most preferred embodiment would consist of a thin titanium layer 21 deposited to the sensing area 65 to act as adhesion layer. Preferably the adhesion layer 21 is of a thickness in the range 3-30 nm, and more preferably in the range of 5-15 nm, with about 10 nm being the most preferred embodiment. A conductive gold or platinum film 30 is deposited on top of the adhesion layer 21 to form the electrode. Preferably the electrode 30 is of a thickness in the range 10-300 nm, and more preferably in the range of 50-200 nm, with about 50-150 nm being the most preferred embodiment. Another thin titanium adhesion layer 20 is located on the electrode layer, and is preferably of similar characteristics as adhesion layer 21. A barrier layer 40 of niobium or tantalum is located on the adhesion layer 20. Preferably the barrier layer 40 is of a thickness in the range 25-300 nm, and more preferably in the range of 50-250 nm, with about 150 nm being the most preferred embodiment. An outer layer 50 of DLC is placed on top of the barrier layer. Preferably the outer layer 50 is of a thickness in the range 10-500 nm, and more preferably in the range of 50-250 nm, with about 150 nm being the most preferred embodiment. Notably, adhesion layers 20 and 21 are optional.

The exact composition of the DLC is a matter of technical choice. Common experience in thin film development suggest numerous optional dopants or surface treatments ranging from parts per million to several percent of nitrogen or various metals. Fluorine dopants have been considered from trace levels through to 67 atomic percent (perfluoroalkanes) with only low (<20%) concentrations being practical. Boron doping up to 1% is especially of interest to provide a conducting version of a DLC coating known as boron-doped diamond. Such films are especially applicable to the integration of electrochemical methods to an AWD.

The unterminated dangling bonds of the carbon film will react with hydrogen in the air (from acidic moisture) to become passivated. If desired other layers may be attached to the outer DLC layer. Prior to this passivation the surfaces will react with bromo-, iodo-, and chloro-functional molecules including iodo-fluoroalkane, chloro-silanes, and bromo-perfluoropolyethers, by way of non-limiting example. Silane chemistry is a well known method of introducing a wide diversity of functional surfaces including carboxyl and amine groups. The use of peptide bonds to attach bioreceptors for biochemically selective sensing or polymer films for chemically-selective sensing is then a well-know extension.

In particular, functional chloro-silanes ($ClSi(CH_3)_2$-R) react with a hydrogen-terminated carbon surface by forming a C—Si bond and evolving HCl. The functional group, R, is then used in a myriad of well known chemical synthesis steps. While not as chemically or abrasion resistant as the DLC surface, the covalently attached monolayers are quite robust.

In one preferred embodiment chemically selective probes are attached to the DLC surface. It is possible to terminate the freshly deposited DLC film with functional chemical groups including amine and carboxyl groups, allowing further chemically specific layers to be attached. Thus, by way of example, using a commonly available compound such as $Cl(CH3)2-Si—(CH2)2NH2$ to attach —$NH2$ to the surface, it is then possible to use peptide bond formation to attach a bioreceptor. Succinnic acid anhydride is used to form —NH-C=O—(CH2)2-COOH surface functional groups. These acid residues may then be joined to —NH2 residues on a protein (antibody, antigen, enzyme) or synthetically attached to a DNA or peptide nucleic acid (PNA) probe. The final coupling stage is catalyzed using a water-soluble carbo-diimide. Alternatively the carboxyl groups can be reacted with amines in a polymer film having a preferential absorption of a target measurand. One such example is to select a polymer having preferential absorption of chlorinated hydrocarbons for environmental sensing. Another example is a hydrophilic coating for measuring water content in gasoline and other fuels.

Sensors in general, and liquid phase sensors in particular are often used in harsh environments such as crude oil slurries and drilling mud for in well measurements, abrasive inks, acids, and the like. Long time stability of such sensors depends largely on the capability to keep the smoothness and consistent characteristics of the sensing area or areas. The utilization of the coating as described in conjunction with an AWD type sensor offers significant advantages as it allows the sensor to operate in areas which heretofore lacked easy continuous coverage of the sensed parameters. By way of example, uses enabled or improved by an AWD sensor coated in accordance with the teachings of the present invention include monitoring "cutting fluids" in metal-working applications, process control in the manufacture of titania and other slurries, oil production applications including drilling mud, paper coating processes, highly caustic chemical processes, and the like. While the benefits are most notable for harsh environments such as those described above, less demanding sensing applications will also benefit from longer sensor lifetime, including for example automotive sensors such as engine oil monitoring.

A preferred process of creating a coating is shown in FIG. 3. Firstly, the substrate—either the sensor sensing area, or any other surface to be coated, is cleaned 300. Typically this step is carried out utilizing solvent washes and water rinses, followed preferably by an oxygen/argon plasma etch in a vacuum.

Optionally, a first adhesion layer 21 comprising of chromium (Cr) or titanium (Ti) is then deposited 305 on the surface. Zirconium (Zr) is also applicable and hafnium (Hf), niobium (Nb) and tantalum (Ta) are suitable in some cases, but chromium is most prevalent for moderate temperatures, and titanium is considerate most suited for elevated temperatures.

An electrode 30 is then deposited 310 over the first adhesion layer, if such layer is used. As described, for a conductive electrode there are numerous choices including platinum (Pt), palladium (Pd), gold (Au), silver (Ag), copper (Cu) and aluminum (Al), as well as more exotic conductors such as ruthenium (Ru), rhodium (Rh), rhenium (Re), osmium (Os), and iridium (Ir). Aluminum (Al) is the least expensive material but is sometimes undesirable as it is chemically reactive and has high diffusion into adjacent materials. Platinum (Pt) and palladium (Pd) are the most stable selections and gold (Au) is the most commonly used and is the preferred embodiment for all but the harshest environments and temperatures.

Note that the electrode region may be selectively deposited using various lithography methods to only cover a specific pattern on the surface. Such patterns may include transducers, electrochemical electrodes, circuits, antennae and the like.

Optionally a second adhesion layer 20 may be deposited 215 between the electrode and the barrier layer, as was described for the first adhesion layer 21, however in some applications the vanadium, molybdenum, niobium or tantalum of the barrier layer adhere directly to the electrode layer.

As described, a barrier layer 40 is deposited 220 over the electrode and if applicable the second adhesion layer, to isolate the electrode layer 30 and/or adhesion layer 20 from the outer DLC layer 50. Commonly tungsten (W) and platinum (Pt) are used as barrier metals. However both tungsten and platinum suffer from poor adhesion to DLC. Furthermore, the use of an adhesion layer of titanium or chromium between tungsten and DLC is unacceptable at higher temperatures due to long term inter-diffusion. Therefore the preferred embodiment of this aspect of the invention utilizes niobium or tantalum as barrier layer. Vanadium and molybdenum may also be suitable.

A DLC layer is then deposited 225 over the barrier layer, to provide the desired mechanical characteristics. Proper selection of process allows the barrier metal surface to provide excellent direct adhesion of the DLC by forming a thin (typically circa 5 nm), stable transition region of carbide alloy.

In the most preferred embodiment, the layers are thus in order starting in the base material 10, a first titanium adhesion layer 21 about 3-30 nm thick, a gold or platinum electrode layer 30 about 10-300 nm thick, a second titanium adhesion layer 20 about 3-30 nm thick, a tantalum barrier layer 40 about 25-300 nm thick and the final DLC layer about 10-500 nm thick.

In yet another aspect of the invention the coating is applied to passivate at least one electrode deposited on material such as a printed circuit board or other material exposed to corrosive, explosive or other harsh environment. Further application of the coating according to the present invention is for providing coatings for tools, and the like.

The following is a list of materials that are preferred for practicing the invention. It should be noted however that the list relates only to preferred materials and should not be construed as limiting in nature.

Adhesion promoters for optional adhesion layers 20 and 21: titanium, zirconium, chromium, vanadium, niobium, tantalum.

Conductive electrode layer 30: platinum, palladium, gold, silver, copper, aluminum. Alloys of the above are also widely used, as well as osmium, iridium and the like, and the invention extends thereto.

Barrier layer 40: Tantalum, niobium, vanadium, molybdenum.

The skilled in the art will recognize that the preferred embodiments provided above are provided by way of non-limiting examples and that the teaching of these specifications will allow the skilled to produce a variety of materials to answer specific requirements for which the coating or the coated device are required to meet. Similarly, the skilled in the art will recognize that while the specifications are primarily directed to sensors, and even more particularly oftentimes to AWD type sensors, the coating described is highly applicable to many other applications that may benefit from the mechanical strength and smoothness of a DLC layer, and yet suffer from poor adhesion characteristics to DLC. Thus the invention should be viewed as extending to such embodiments and similar derivatives of the teaching provided herein. Various material combinations answering the specific needs, as well as different coating thicknesses will likely be applied to by the skilled artisan to obtain specific characteristics. However the invention extends to such modifications as well.

While there have been described what are at present considered to be the preferred embodiments of this invention, it will be obvious to those skilled in the art that various other embodiments, changes, and modifications may be made therein without departing from the spirit or scope of this invention and that it is, therefore, aimed to cover all such changes and modifications as fall within the true spirit and scope of the invention, for which letters patent is applied.

What is claimed is:

1. A coated Acoustic Wave Device (AWD) based sensor, the sensor comprising at least one piezoelectric plate having two opposing faces, one of said faces having a sensing area, the sensor having a coating applied to the sensing area, the coating comprises:

A first electrode disposed on said sensing area;

a barrier layer disposed over said first electrode, said barrier layer comprising at least one metal selected from the group consisting of tantalum, niobium, vanadium, molybdenum, or a combination thereof; and, an abrasive resistant layer comprising Diamond-Like Carbon (DLC) disposed over said barrier layer.

2. A coated acoustic wave device sensor according to claim 1, wherein the coating further comprises an adhesion layer disposed between said electrode and said sensing area.

3. A coated acoustic wave device sensor according to claim 1, wherein the coating further comprises an adhesion layer disposed between said electrode and said barrier layer.

4. A coated acoustic wave device sensor according to claim 2, wherein any of said adhesion layers comprises a metal selected from a group consisting of titanium, zirconium, chromium, vanadium, niobium, tantalum, or a combination thereof.

5. A coated acoustic wave device sensor according to claim 2, wherein said first electrode comprises a metal selected from a group consisting of platinum, palladium, gold, silver, copper, aluminum, ruthenium, rhenium, osmium, iridium, or a combination thereof.

6. A coated acoustic wave device sensor according to claim 1, wherein the DLC comprises boron doped diamond.

7. A coated acoustic wave device sensor according to claim 1, wherein the acoustic wave device sensor further comprises a second electrode disposed on the face opposite the face comprising said sensing area, for forming a parallel plate resonator with said first and second electrodes.

8. A coated acoustic wave device sensor according to claim 7 further comprising a third electrode disposed on the face opposite the face comprising the sensing area, wherein:

said first and second electrodes forming an input parallel resonator;

said first and third electrode forming an output parallel resonator;

said input and output resonators being sufficiently close to couple acoustic energy from the input resonator into the output resonator, for forming a multi-pole coupled resonator filter.

9. A coated acoustic wave device as claimed in claim 1, further comprising at least one chemically selective probe probes coupled to said DLC layer.

10. A coated acoustic wave device as claimed in claim 1 wherein the first electrode is connected as the working electrode in an electrochemical measurement.

11. A coated acoustic wave device sensor according to claim 3, wherein any of said adhesion layers comprises a metal selected from a group consisting of titanium, zirconium, chromium, vanadium, niobium, tantalum, or a combination thereof.

12. A coated acoustic wave device sensor according to claim 3, wherein said first electrode comprises a metal selected from a group consisting of platinum, palladium, gold, silver, copper, aluminum, ruthenium, rhenium, osmium, iridium, or a combination thereof.

13. A coated acoustic wave device sensor according to claim 4, wherein said first electrode comprises a metal selected from a group consisting of platinum, palladium, gold, silver, copper, aluminum, ruthenium, rhenium, osmium, iridium, or a combination thereof.

14. A coated acoustic wave device sensor according to claim 4, wherein the DLC comprises boron doped diamond.

15. A coated acoustic wave device sensor according to claim 5, wherein the DLC comprises boron doped diamond.

* * * * *